United States Patent [19]

Tanaka

[11] Patent Number: 5,737,059
[45] Date of Patent: Apr. 7, 1998

[54] APPARATUS FOR MEASURING THE REFRACTIVE POWER OF AN OPTICAL SYSTEM USING FOURIER-TRANSFORM

[75] Inventor: Takumi Tanaka, Hiratsuka, Japan

[73] Assignee: Nikon Corporation, Tokyo, Japan

[21] Appl. No.: 640,191

[22] Filed: Apr. 30, 1996

[30] Foreign Application Priority Data

May 10, 1995 [JP] Japan .................................. 7-112025

[51] Int. Cl.[6] .................................................. A61B 3/10
[52] U.S. Cl. .................................... 351/214; 351/205
[58] Field of Search ................................. 351/211, 221, 351/206, 205, 246, 214

[56] References Cited

U.S. PATENT DOCUMENTS

| 4,676,612 | 6/1987 | Wada et al. | 351/211 |
| 5,428,414 | 6/1995 | Iwane | 351/214 |

*Primary Examiner*—Hung X. Dang
*Attorney, Agent, or Firm*—Shapiro and Shapiro

[57] ABSTRACT

An apparatus for measuring the refractive power of an optical system has a scan optical system for scanning a fundus with slit light beams, a measuring optical system for taking the slit light beams reflected from the fundus of the examined eye, a plurality of light receivers for detecting the slit light beams taken in by the measuring optical system, and a calculator for obtaining Fourier spectrums by Fourier-transforming detection signals of the plurality of light receivers and thus calculating the eye refractive power of the examined eye on the basis of predetermined frequency components of Fourier spectrums of the detection signals.

7 Claims, 4 Drawing Sheets

APPARATUS FOR MEASURING THE REFRACTIVE POWER OF AN OPTICAL SYSTEM USING FOURIER-TRANSFORM

BACKGROUND OF THE INVENTION

1. Field of the Invention

The present invention relates to an apparatus for measuring the refractive power of an optical system.

2. Related Background Art

An apparatus for measuring the refractive power of an optical system has hitherto involved the use of a known optometric method for measuring the refractive power of an eye in an objective manner. The refractive power of the examined eye has hitherto been obtained by horizontally and vertically scanning a fundus of an examined eye with slit beams and detecting the slit beams reflected from the fundus. The slit-beam scanning is attained by rotating a chopper formed with a plurality of slits and irradiating it with the light beams from a light source. As illustrated in FIG. 6, a control arithmetic unit comprises four light receiving elements $71a$–$71d$, and signal amplifiers $82a$–$82d$ for amplifying measurement signals outputted from the respective light receiving elements. The control arithmetic unit also comprises signal separators $83a$–$83d$ for independently extracting scan signal components in the horizontal and vertical directions, phase difference detectors 85X and 85Y for obtaining a phase difference between corresponding extracted signals, an arithmetic unit 86 and a control unit 87. Note that the signals outputted from the individual light receiving elements contain higher harmonic components as noises in addition to the actually required scan signal components both in the horizontal direction and in the vertical direction, and therefore the signal separators $83a$–$83d$ eliminate those noises when extracting the signals.

There arise a variety of problems inherent in the prior art control arithmetic unit.

First, the above-mentioned signal separators $83a$–$83d$ are hard to provide with a high stability and accuracy.

For example, as illustrated in FIG. 3, when the chopper 3 is formed with four horizontal scan slits ($30a$–$30d$) and six vertical scan slits ($32a$–$32f$) and is rotated at 6,000 rpm, a horizontal scan frequency is 400 Hz, and a vertical scan frequency is 600 Hz. These two frequencies are very close to each other. Accordingly, there must be employed a filter exhibiting a remarkably electrically high selectivity (a so-called high Q) in order to extract only the horizontal or vertical scan signal components out of the measurement signals obtained by the above-mentioned chopper.

Such a filter generally has, however, a steep characteristic of phase variation of a central frequency, i.e., a separation frequency. Accordingly, this filter not only requires the parts to be used for a high precision but also is sensitive to variation in ambient environments (such as temperature, humidity, etc.). The same filter is therefore hard to deal with in terms of the stability.

The filter selectivity can be decreased in consideration of the stability of the apparatus. In this case, however, the scan signal components exclusive of the above-mentioned are mixed in the scan signal components to be extracted. The mixture of such signal components may cause a beat due to the signals on the corresponding side and phase fluctuations in the respective signals outputted by the signal separators $83a$–$83d$. Such phase fluctuations may lead to a scatter of the phase difference data. For this reason, it has hitherto been required that numerous pieces of phase difference data be collected and some contrivance for reducing the scatter by an averaging process or the like be needed to obtain a stable phase difference. In addition, such collecting/averaging process of the phase difference data is, of course, an obstacle against the reduction in the measuring time.

Further, there have hitherto been in some cases contrived measures for reducing a burden on the filter used for the signal separators $83a$–$83d$ by increasing a ratio of the number of horizontal scan slits to the number of vertical scan slits (e.g., the number of the horizontal scan slits is set to 4, while the number of vertical scan slits is set to 10). In this case, however, a refractive power measurable range of the apparatus is narrowed, the measurement signals before the separation still contain a higher harmonic components of fundamental frequencies of the respective scan signals and cross modulation components of the two, and no substantial effect can be seen.

A second problem is that there are, as illustrated in FIG. 6, eight channels for receiving the signals after being separated so as to be capable of corresponding to horizontal scan signals $84ax$–$84dx$ and vertical scan signals $84ay$–$84dy$. If there are prepared such a number of channels, this may result in a scale-up of the circuits of the phase difference detectors $85x$ and $85y$.

For instance, each of the phase difference detectors $85x$ and $85y$ is constructed of a waveform shaping circuit for shaping a waveform of a separated analog sine wave signal and a digital phase difference counter (e.g., a 16-bit counter circuit) for obtaining a phase difference from the output signals of the waveform shaping circuit. These constructive elements are all needed for the eight channels.

SUMMARY OF THE INVENTION

It is a primary object of the present invention to provide an apparatus for measuring the refractive power of an optical system that is capable of calculating eye refractive power data with a high accuracy in a short period of time.

To this end, an apparatus for measuring the refractive power of an optical system can comprise a scan optical system for scanning a fundus with slit light beams, a measuring optical system for taking the slit light beams reflected from the fundus of an examined eye, a plurality of light receivers for detecting the slit light beams taken in by the measuring optical system, end a calculator for obtaining Fourier spectrums by performing Fourier-transform on detection signals of the plurality of light receivers and thus calculating the eye refractive power of the examined eye on the basis of predetermined frequency components of Fourier spectrums of the detection signals.

According to the present invention, the calculator obtains the Fourier spectrums by effecting the Fourier-transform on the respective detection signals of the plurality of light receivers. The calculator calculates the eye refractive power of the examined eye on the basis of the predetermined frequency components of the Fourier spectrums of the individual detection signals. That is, an electrical filter extracts the predetermined frequency components of the respective detection signals. The extraction of the frequency components becomes easier and an extraction accuracy are more improved than in the prior art for calculating the eye refractive power on the basis of the extracted frequency components.

Each of the plurality of light receivers outputs an analog signal obtained when detecting the slit light beam. In this case, the calculator, for example, converts the plurality of analog signals into digital signals by sampling the analog signals and uses the converted digital signals as the detection signals. Further, the calculator obtains cross power spectrums of at least two analog signals among the plurality of analog signals, calculates a relative phase difference between the two analog signals from phases of frequency components of the cross power spectrums and calculates the eye refractive power on the basis of the relative phase difference. This eliminates the necessity for a fiducial signal for calculating an absolute phase as compared with a case where the eye refractive power is calculated from the absolute phase of each of the Fourier spectrums of the two analog signals.

Note that the scan optical system may perform continuous scanning in a plurality of directions by use of the slit light beams. In this case, the frequency components are frequency components corresponding to periods of respective scans in the plurality of directions.

Furthermore, the optical system comprises a rotary plate formed with a plurality of first and second slits extending in directions different from each other, a driver for rotating this rotary plate, and a light source for irradiating said rotary plate that is being rotated with light. In this case, the calculator unit sets a multiple of a greatest common divisor of the number of the first slits and the number of the second slits, as a number of samples when sampling the analog signals. This may makes it easier to set a time window when sampling.

As discussed above, according to the present invention, there is no necessity for a scatter reducing process when calculating the phase difference. Hence, the measuring time is reduced, and the measuring accuracy is improved. Moreover, it is simple to set and change the sampling frequency and the number of samples, and the apparatus can therefore correspond to a variety of needs. In addition, since the detection signals of the light receiving elements are directly digitally processed without using any band filter, etc., it is possible to make the apparatus stable and resistive to changes with a passage of time and variations in the ambient environment.

DESCRIPTION OF THE PREFERRED EMBODIMENTS

Preferred embodiments of the present invention will hereinafter be discussed with reference to the accompanying drawings.

Figures 1, 2:
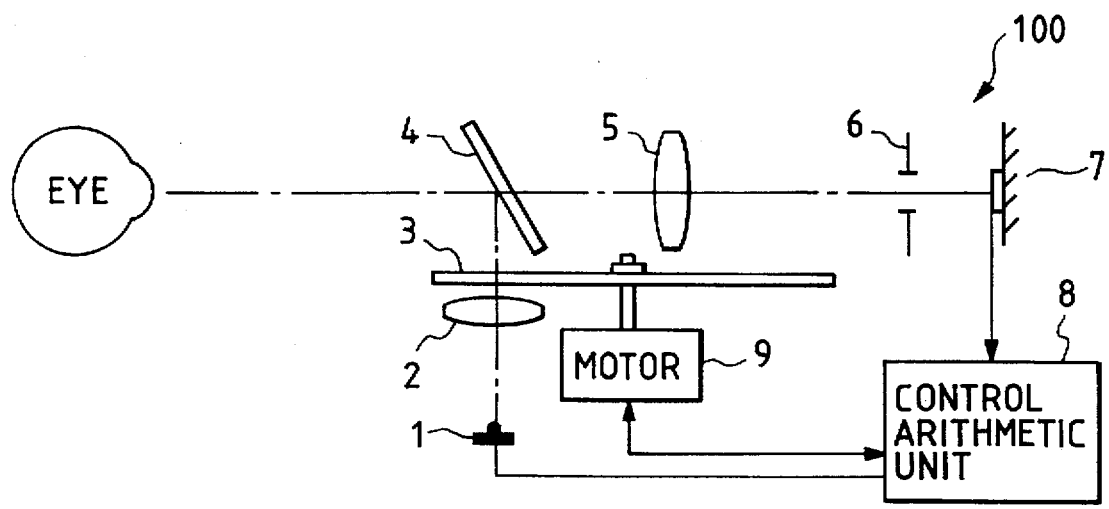
FIG. 1 is a diagram showing a construction of an objective eye refractive power measuring apparatus by way of one embodiment of the present invention.
FIG. 2 is a plan view illustrating a lay-out example of light receiving elements used in the objective eye refractive power measuring apparatus shown in FIG. 1.

As illustrated in FIG. 1, an objective refractive power measuring apparatus 100 includes a light source 1 for emitting light beams required for a measurement, and a collimator lens 2 for collimating the light beams emitted from the light source 1. The measuring apparatus 100 also includes a chopper 3 having a plurality of geometrically formed slits, a motor 9 for rotating the chopper 3, and a half-mirror 4 which guides the light beams (slit beams) passing through the rotating chopper 3 to an examined eye and transmits the light beams reflected from the examined eye. The measuring apparatus 100 further includes a lens 5 for guiding the slit beams penetrating the half-mirror 4, a diaphragm 6, and a sensor 7 consisting of a plurality of light receiving elements 71a–71d (see FIG. 2) for detecting the slit beams obtained through the lens 5.

Figure 3:
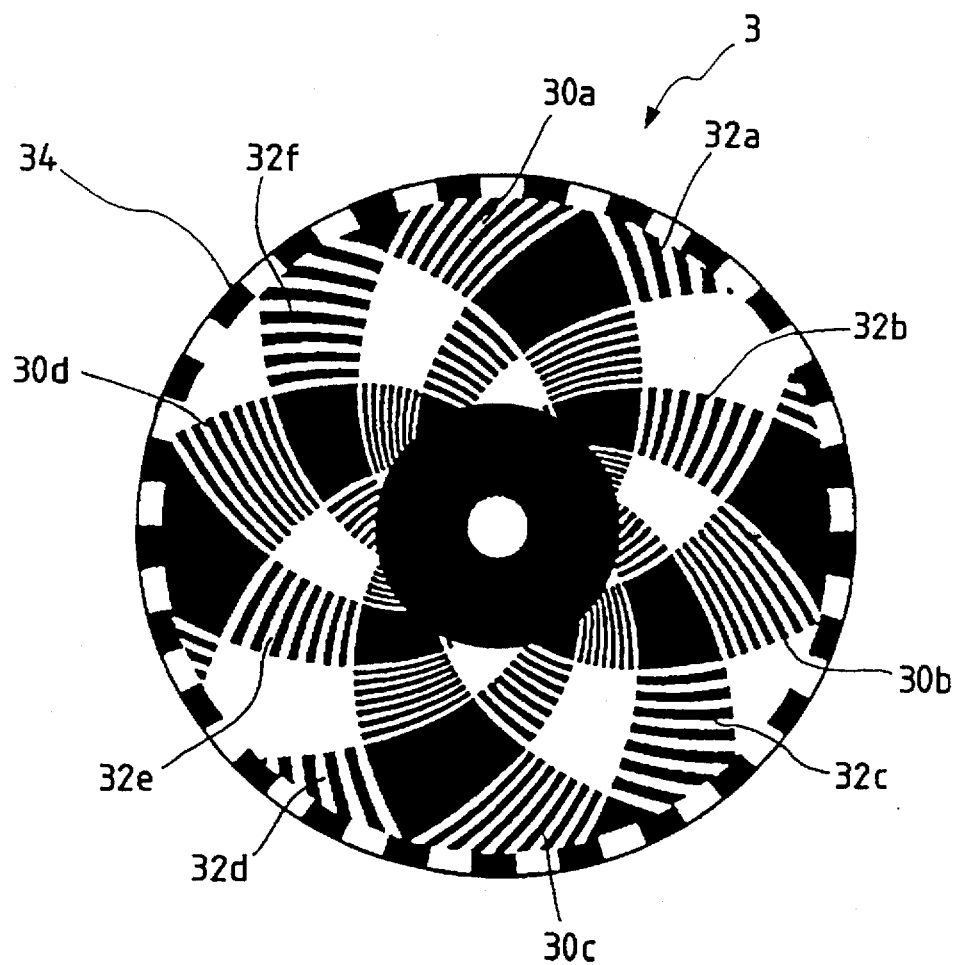
FIG. 3 is a plan view illustrating one example of a chopper used in the objective eye refractive power measuring apparatus shown in FIG. 1.

The chopper 3 is, as shown in FIG. 3, formed respectively with four slits 30a–30d for a horizontal scan and six slits 32a–32f for a vertical scan with spiral patterns. Further, an outer periphery of the chopper 3 is formed with a pattern 34 for detecting a rotating speed of the chopper 3. The numbers of the slits are not particularly limited to those described above but are set desirably in an n-to-n.((2k+1)/2) relationship to attain an easier separation (which will hereinafter be explained in detail) of measuring signals when performing the horizontal and vertical scanning.

The light receiving elements 71a–71d are, as illustrated in FIG. 2, arranged vertically and horizontally about a point P. Note that an interval between the light receiving elements may be set in a known manner but may not necessarily be an equal interval. Further, there is no necessity of arranging the light receiving elements in a cross shape, and those elements may be arranged in a T-shape.

Configurations other than a control arithmetic unit 8 have been explained thus far, however, the respective constructive requirements disclosed in U.S. Pat. No. 5,428,414 are applicable to those other components.

Next, the control arithmetic unit 8 will be described.

Figure 4:
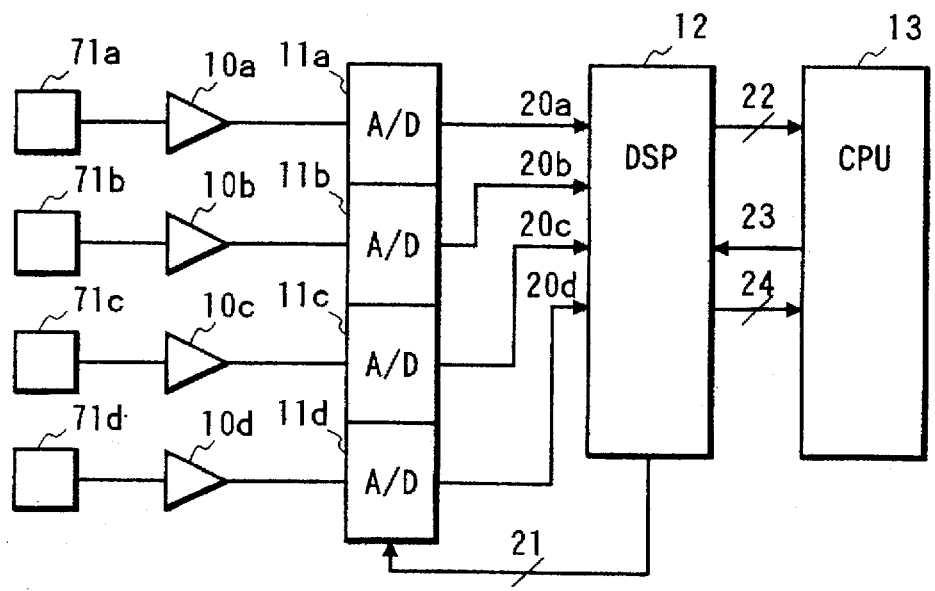
FIG. 4 is a block diagram illustrating one example of a control arithmetic unit used in the objective eye refractive power measuring apparatus shown in FIG. 1.

The control arithmetic unit 8 has, in addition to the control over the light source 1 and the motor 9, a construction shown in FIG. 4, which is characteristic of the present embodiment.

More specifically, the control arithmetic unit 8 incorporates signal amplifiers 10a–10d for amplifying respective analog signals outputted from the light receiving elements 71a–71d, and A/D converters 11a–11d for receiving the thus amplified analog signals and converting them into digital signals. The control arithmetic unit 8 also incorporates a digital signal processor (hereinbelow called a DSP unit) 12 for calculating a phase difference between corresponding analog signals by obtaining a desired Fourier spectrum with an execution of a discrete Fourier transform (DFT) of each of the converted digital signals (20a–20d). The control arithmetic unit 8 further incorporates a CPU 13 for calculating an eye refractive power (specifically, a degree of spherical surface, a degree of column and an axis of column) on the basis of the calculated phase difference.

Herein, a theoretical ground for obtaining the eye refractive power will be elucidated by use of the Fourier spectrum.

Given first is a brief explanation of the fact that a relative phase difference $\phi_{AB}$ between given frequencies f of two analog signals A and B containing these frequencies f is determined by performing the Fourier transform for the analog signals A and B.

The analog signals A and B are Fourier-transformed, thereby obtaining Fourier spectrums thereof. In this case, each Fourier spectrum is generally expressed by a complex number. Accordingly, absolute phases thereof can be expressed by arg[Sa(f)] and arg[Sb(f)], wherein Sa(f) and Sb(f) are respectively the components of the frequencies f of the respective Fourier spectrums of the analog signals A and B. These absolute phases can be obtained based on the known algorithm.

If the absolute phases of the components of the frequencies f of the respective Fourier spectrums can be known, the above-mentioned relative phase difference $\phi_{AB}$ can be obtained the calculation as shown in the formula 1.

$$\phi_{AB} = arg[Sa(f)] - arg[Sb(f)] \quad (1)$$
$$= arg[Sa(f)/Sb(f)]$$

Now, Sb(f) is the complex number, and hence there must exist Sb*(f) as a complex conjugate. Accordingly, the formula 1 can be transformed into the formula 2 by use of this complex conjugate Sb*(f).

$$\phi_{AB} = arg [Sa(f)Sb*(f)/Sb(f)Sb*(f)] \quad (2)$$

If transformed in this way, it follows that the numerator Sa(f) Sb*(f) of the formula 2 expresses so-called cross power spectrums of the signals A and B. On the other hand, the denominator Sb(f) Sb*(f) expresses an auto power spectrum of the signal B. Note that Sa(f) Sb*(f) is the complex number while Sb(f) Sb*(f) is a real number, and it therefore follows that Sb(f) Sb*(f) contains no phase data.

That is, the relative phase difference $\phi_{AB}$ between the frequencies f of the two analog signals A and B containing the frequencies f can be also calculated from the cross power spectrums of the two signals. The relative phase difference $\phi_{AB}$ may be calculated as shown in the formula 1 from the absolute phases (arg[Sa(f)], arg[Sb(f)]). In this case, however, a timing signal serving as a reference is needed. Accordingly, it is more convenient to calculate the relative phase difference $\phi_{AB}$ by use of the cross power spectrums.

An explanation will be again given herein by applying the above-mentioned to the present embodiment.

Note that $f_H$ and $f_V$ are the horizontal/vertical scan frequencies, respectively. For example, as shown in FIG. 3, when the chopper having the four horizonal scan slits and six vertical scan slits is rotated at 6,000 rpm, a horizontal scan frequency is 400 Hz, and a vertical scan frequency is 600 Hz. Further, it is assumed that the Fourier spectrums of the frequencies $f_H$, $f_V$ of the respective analog signals outputted from the light receiving elements 71a–71d are respectively Sa($f_H$), Sb($f_H$), Sc($f_H$), Sd($f_H$), Sa($f_V$), Sb($f_V$), Sc($f_V$) and Sd($f_V$), Further, let dx be the relative phase difference between the analog signals outputted respectively from the light receiving elements 71a and 71b during the horizontal scan (when the slit image moves in the horizontal direction in FIG. 2). Let $\Delta y$ be the relative phase difference between the analog signals outputted respectively from the light receiving elements 71a and 71b during the vertical scan (when the slit image moves in the vertical direction in FIG. 2). Moreover, let $\Delta x$ be the relative phase difference between the analog signals outputted respectively from the light receiving elements 71c and 71d during the horizontal scan and dy be the relative phase difference between the analog signals outputted respectively from the light receiving elements 71a and 71b during the vertical scan.

The fact that the relative phase difference between the two signals is obtained from the cross power spectrums of those signals has already been stated by using the formula 2.

Accordingly, the relative phase differences dx, dy, $\Delta x$ and $\Delta y$ can be individually obtained from the formula 3.

$$dx = Sa(f_H) \: Sb*(f_H)$$
$$dy = Sc(f_V) \: Sd*(f_V)$$
$$\Delta x = Sc(f_H) \: Sd*(f_H)$$
$$\Delta y = Sa(f_V) \: Sb*(f_v) \quad (3)$$

It is to be noted that the formula 3 describes nothing corresponding to the denominator of the formula 2, and this is herein omitted because it includes no phase data as stated earlier.

Then, when the respective relative phase differences are obtained, the eye refractive power (specifically the degree of spherical surface, the degree of column and the axis of column) of the examined eye can be calculated by solving the predetermined known simultaneous equations. The details of the simultaneous equations are shown in U.S. Pat. No. 5,428,414 and therefore herein omitted.

The theoretical ground for obtaining the eye refractive power by use of the Fourier spectrum has been elucidated so far. In this embodiment, however, the analog signals are converted into the digital signals by employing the A/D converters 11a–11d, and thereafter the digital signal processing is exclusively carried out. Hence, the Fourier spectrum treated actually is not continuous but discrete.

Therefore, a discrete Fourier transform (DFT) used in this embodiment will be also touched upon. Incidentally, the Fourier spectrum can be obtained by not only the DFT algorithm but also a generally known FFT algorithm. Those algorithms are only different in terms of a calculation process, but the final results are the same. Accordingly, either of those algorithms may be employed.

First, the definitions will be given as follows:

x(t): signal of the time t, and x(n): sample data of x(t).

x(t) corresponds to the analog signal outputted from each of the light receiving elements 71a–71d, while x(n) corresponds to the digital data sampled by each of the A/D converters 10a–10d.

Then, for example, when N-pieces of data are sampled at a sampling interval T (=1/$f_s$) from x(t), X(k) representing the frequency component of the Fourier spectrum can be expressed as shown in the formula 4.

$$X(k) = \sum_{n=0}^{N-1} x(n) \exp(-j2\pi nk/N) \quad (4)$$
$$k = 0, 1, 2, \ldots, N - 1$$

where j is the imaginary number unit, and $j^2 = -1$. Note that $f_s$ represents the sampling frequency.

Further, the frequency component (=f) bears a relationship given by the following formula 5.

$$f = (k/NT) = k(f_s/N) \quad (5)$$

Namely, if the sampling frequency $f_s$ is properly combined with the sample number N, the Fourier spectrum containing a desired frequency component can be obtained.

Accordingly, when acquiring the above-mentioned relative phase differences dx, dy, $\Delta x$, $\Delta y$, the sampling frequency $f_s$ and the sample number N are set so that the Fourier spectrum contains the components of the desired frequencies $f_H$ and $f_V$ (specifically, 400 Hz and 600 Hz).

Incidentally, if the data are sampled with a window having a finite length from the continuous signals (specifically, the analog signals of the light receiving elements 71a–71d) on the time base, the digital signal process can be facilitated by sampling the number of pieces of data each having a time length of a multiple of natural number of a signal repetitive period, whereby a data processing time can be reduced.

Further, even when using no window having the length of a multiple of the signal frequency, a discontinuity of the signal is corrected by a so-called window function, and the Fourier spectrum may be thus obtained. As a matter of course, the present invention is not conditioned by a difference therebetween.

Now, in the majority of cases, the DFT or FFT arithmetic process is generally used for the audio signal and a digital filter, etc. In such a case, however, it is a common practice that all the frequency components within signal bands dealt with are to be processed. Accordingly, the data processing time inevitably increases.

In accordance with this embodiment, however, as obvious from the description made thus far, only eight pieces of Fourier spectrums to be calculated, such as $Sa(f_H)$, $Sa(f_V)$, $Sb*(f_H)$, $Sb*(f_V)$, $Sc(f_H)$, $Sc*(f_V)$, $Sd*(f_H)$, $Sd*(f_V)$, are sufficient. This makes the arithmetic quite easy and the processing time thereof extremely short for the arithmetic unit for a special use of the digital data processing which is represented by DSP.

Referring back to FIG. 4, a flow of processing by the control arithmetic unit 8 will be next explained.

The signals outputted from the light receiving elements 71a–71d are amplified by the signal amplifiers 10a–10d and become signals exhibiting levels enough for the A/D converters 11a–11d. Note that the signal amplifiers 10a–10d include antialiasing filters well known in the sampling theorem, whereby aliasing noise components are prevented from mixing in the conversion data of the A/D converters 11a–11d. The A/D converters 11a–11d use sampling clock signals after receiving start-of-conversion control signals 21 from the DSP unit 12 to perform the A/D conversions. Measurement signals 20a–20d converted into the digital data by the A/D converters 11a–11d are supplied to the DSP unit 12. The DSP unit 12, upon receiving a start-of-processing command 23 from the CPU 13, performs the above-mentioned DFT arithmetic operation by use of the measurement signals 20a–20d, thus calculating necessary phase difference data. The CPU 13 monitors a status of the DSP unit 12 (on lines 24) and, after finishing the arithmetic process, receives the phase difference data (on lines 22). The CPU 13 calculates the degree of spherical surface, the degree of column and the axis of column on the basis of the above data.

Note that a light receiving element for detecting an alignment of an optical axis of the apparatus with an optical axis of the examined eye is, though not shown, disposed at the center of the sensor 7 surrounded by the light receiving elements 71a–71d. The CPU 13 is so constructed as to issue the start-of-processing command 23 to the DSP unit 12 when well aligned.

Furthermore, the DSP unit 12 is previously stored with specific values of the sampling frequency and the number of samples (which have already been described by use of the formula 5 and are therefore herein omitted), and is so constructed as to be capable calculating the Fourier spectrums required. As a matter of course, if those specific values are changed, the apparatus can correspond to systems of a variety of specifications.

Incidentally, in accordance with this embodiment, the DSP unit 12 and the CPU 13 are independently constructed but are not confined to this construction. The DSP unit 12 may be constructed to incorporate a function of the CPU 13, and conversely the CPU 13 may be constructed to incorporate the digital signal processing function of the DSP unit 12.

Figure 5:
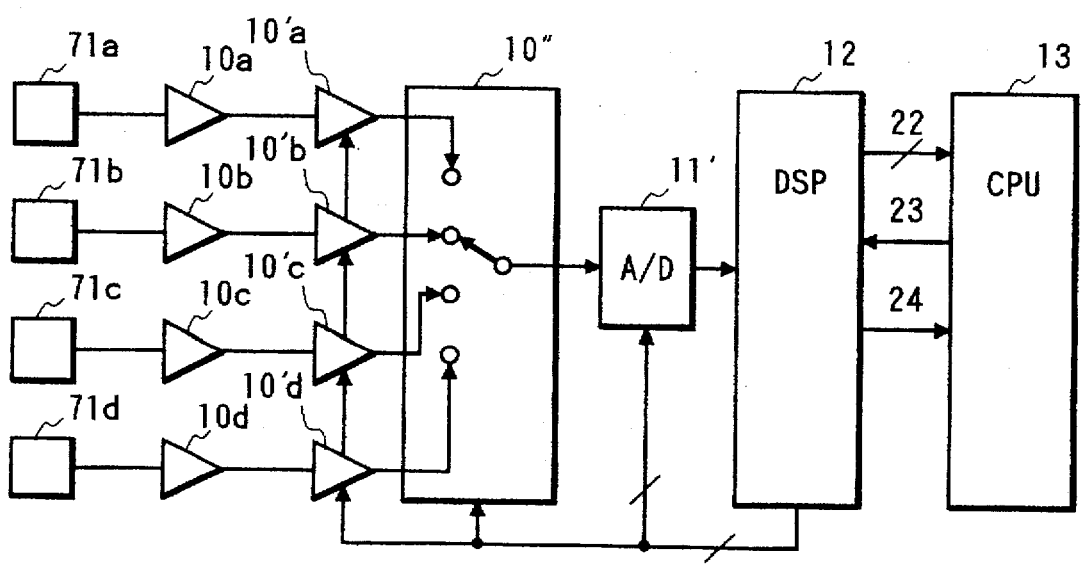
FIG. 5 is a block diagram illustrating another example of the control arithmetic unit used in the objective eye refractive power measuring apparatus shown in FIG 1.
Figure 6:
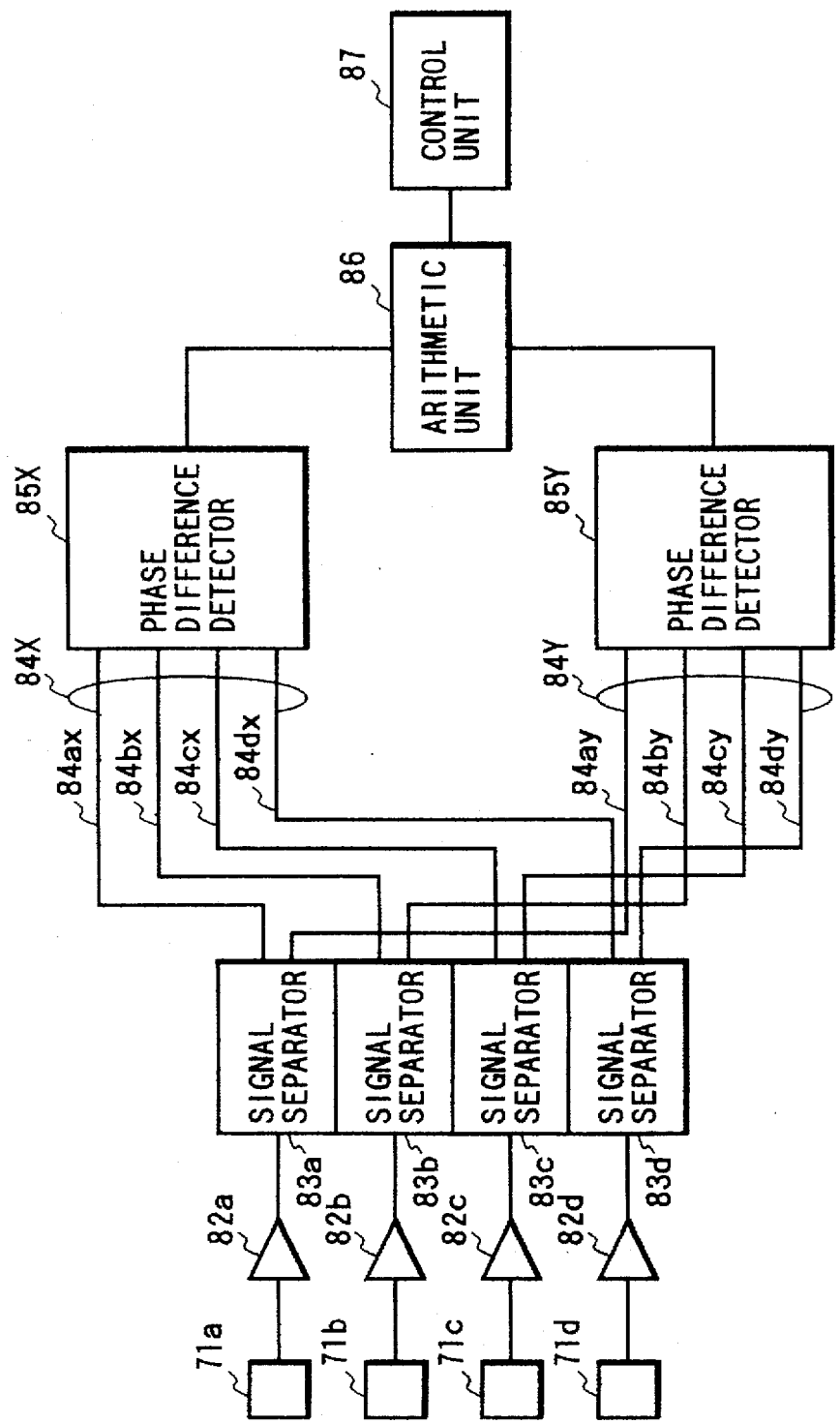
FIG. 6 is a block diagram illustrating one example of a control arithmetic unit used in a prior art objective eye refractive power measuring apparatus.

Further, as illustrated in FIG. 5, there may be provided a single A/D converter 11' and disposed sample & holds 10'a–10'd and an analog multiplexer 10" anterior to the A/D converter 11'.

In this case, the DSP unit 12 simultaneously samples and holds the measurement signals of the signal amplifiers 10a–10d in accordance with the command issued from the CPU 13. Next, the measurement signals are sequentially supplied to the A/D converter 11' by controlling the analog multiplexer 10".

If constructed as illustrated in FIG. 5, a sampling velocity is slightly slower than by the construction shown in FIG. 4, and consequently the time needed for the measurement increases to some extent. Since the single A/D converter may suffice, however, the costs may be reduced.

Incidentally, a further modification of the construction shown in FIG. 5 can be considered such that the sample & holds 10'a–10'd are omitted, and the signals are sequentially sampled by controlling the analog multiplexer 10". When the output signals of the signal amplifiers 10a–10d are sampled in such a sequence as 10a, 10b, 10c and 10d, the digital data respectively become pieces of 0-, 1-, 2- and 3-sample delay data, and hence a process taking these delays into consideration is required.

Further, the phase difference needed for the apparatus are the relative phase differences between the light receiving elements 71a, 71b and between the light receiving elements 71c, 71d. Therefore, two sets of A/D converters 11' may be provided. One A/D converter simultaneously samples the outputs of the signal amplifiers 10a and 10b, while the other A/D converter simultaneously samples the outputs of the signal amplifiers 10c and 10d, whereby an intricacy of the data processing is more relieved.

This invention being thus described, it will be obvious that the some may be varied in same ways. Such variations are not to be regarded as a departure from the spirit and scope of the invention, and all such variations as would be obvious to one skilled in the art are intended to be included within the scope of the following claims.

What is claimed is:

1. An apparatus for measuring refractive power of an optical system, comprising:

a scan optical device for scanning the optical system with slit light beams at predetermined frequencies;

a measuring optical device for taking in slit light beams reflected from said optical system;

a plurality of light receivers for detecting the slit light beams taken in by the measuring optical device; and a calculator for obtaining Fourier spectrums by performing a Fourier-transform on detection signals of said plurality of light receivers and thus calculating the refractive power of said optical system based on components of said Fourier spectrums corresponding to said predetermined frequencies.

2. The apparatus for measuring refractive power of an optical system according to claim 1, wherein each of said plurality of light receivers outputs an analog signal obtained when detecting a slit light beam, and said calculator converts the plurality of analog signals into digital signals by sampling the analog signals and uses the converted digital signals as the detection signals.

3. The apparatus for measuring refractive power of an optical system according to claim 2, wherein said calculator obtains cross power spectrums of at least two analog signals among the plurality of analog signals, calculates a relative phase difference between the two analog signals from phases of frequency components of the cross power spectrums and calculates the refractive power based on the relative phase difference.

4. The apparatus for measuring refractive power of an optical system according to claim 2, wherein the scan optical device comprises a rotary plate formed with a plurality of first and second slits extending in directions different from each other, a driver for rotating said rotary plate, and a light source for irradiating said rotary plate that is being rotated with light, and wherein said calculator sets a multiple of a greatest common divisor of the number of first slits and the number of second slits, as a number of samples when sampling the analog signals.

5. The apparatus for measuring refractive power of an optical system according to claim 1, wherein said scan optical device performs continuous scanning in a plurality of directions by use of the slit light beams, and said components are components corresponding to periods of respective scans in the plurality of directions.

6. An apparatus for measuring refractive power of an optical system, comprising:

a projection optical device for projecting light beams into said optical system at predetermined scan periods;

a plurality of light receivers for receiving said light beams reflected by said optical system, and for outputting respective detection signals;

a computer for Fourier-transforming said detection signals, and for obtaining respective Fourier spectrums including frequency components corresponding to said predetermined scan periods; and a calculator for computing, based on said Fourier spectrums, phase differences between detection signals having a correspondence relationship, and for calculating refractive power of said optical system based on said computed phase differences.

7. An apparatus according to claim 6, wherein said computer obtains said Fourier spectrums, including the frequency components corresponding to said predetermined scan periods, based on sampling frequencies for sampling said detection signals from said light receivers and numbers of said detection signals to be sampled from said light receivers.

\* \* \* \* \*